(12) United States Patent
Yang et al.

(10) Patent No.: US 12,293,831 B2
(45) Date of Patent: May 6, 2025

(54) ARTIFICIAL INTELLIGENT SYSTEM FOR MANAGING A POULTRY HOUSE

(71) Applicant: ACADEMIA SINICA, Taipei (TW)

(72) Inventors: Wen-Chin Yang, Taichung (TW); Yang-Han Lee, Taoyuan (TW); Yu-Chuan Liang, Taipei (TW); Frederick Kin Hing Phoa, New Taipei (TW); Lee-Tian Chang, Taichung (TW); Cheng-Chih Hsu, Taipei (TW); Jia-Kun Chen, New Taipei (TW); Shau-Ping Lin, Taipei (TW); Chiao-Ling Hsiao, Taichung (TW)

(73) Assignee: ACADEMIA SINICA, Taipei (TW)

( * ) Notice: Subject to any disclaimer, the term of this patent is extended or adjusted under 35 U.S.C. 154(b) by 339 days.

(21) Appl. No.: 17/782,595

(22) PCT Filed: Dec. 2, 2020

(86) PCT No.: PCT/US2020/062932
§ 371 (c)(1),
(2) Date: Jun. 3, 2022

(87) PCT Pub. No.: WO2021/113391
PCT Pub. Date: Jun. 10, 2021

(65) Prior Publication Data
US 2023/0010294 A1    Jan. 12, 2023

Related U.S. Application Data

(60) Provisional application No. 62/944,949, filed on Dec. 6, 2019.

(51) Int. Cl.
*G16H 50/80* (2018.01)
*A01K 1/00* (2006.01)
(Continued)

(52) U.S. Cl.
CPC .......... *G16H 50/20* (2018.01); *A01K 1/0047* (2013.01); *A01K 31/18* (2013.01); *A01K 31/22* (2013.01); *G16H 50/80* (2018.01); *C12Q 1/04* (2013.01)

(58) Field of Classification Search
CPC ...... G16H 50/20; G16H 50/80; A01K 1/0047; A01K 31/18; A01K 31/22; C12Q 1/04
See application file for complete search history.

(56) References Cited

U.S. PATENT DOCUMENTS 8,915,215 B1    12/2014  Helgeson
2010/0198023 A1  8/2010  Yanai et al.
(Continued)

FOREIGN PATENT DOCUMENTS

WO    2018/225107 A1    12/2018

OTHER PUBLICATIONS

International Search Report issued in PCT/US2020/062932, Mar. 10, 2021 (10 pages).

*Primary Examiner* — Michael W Choi
(74) *Attorney, Agent, or Firm* — HSML P.C.

(57) ABSTRACT

A system for use in a poultry house includes a control server, a network gateway disposed in the poultry house and equipping with a wireless communication capability; a movable sensor module disposed in the poultry house, wherein the movable sensor module is movable within the poultry house for obtaining a plurality of environmental parameters associated with specific locations within the poultry house, and a sampling machine disposed in the poultry house for obtaining a sample of poultry waste on the ground of the poultry house. The movable sensor module transmits the environmental parameters to the network gateway, and the
(Continued)

network gateway transmits the environmental parameters to the control server for processing the environmental parameters.

25 Claims, 14 Drawing Sheets

(51) Int. Cl.
*A01K 31/18* (2006.01)
*A01K 31/22* (2006.01)
*G16H 50/20* (2018.01)
*C12Q 1/04* (2006.01)

(56) References Cited

U.S. PATENT DOCUMENTS

| | | | |
|---|---|---|---|
| 2016/0120144 A1* | 5/2016 | Kim | A01K 1/0052 |
| | | | 119/436 |
| 2017/0127622 A1 | 5/2017 | Hong | |
| 2017/0280687 A1 | 10/2017 | Vrabete et al. | |
| 2019/0107621 A1* | 4/2019 | Küking | G01S 17/04 |
| 2019/0141914 A1* | 5/2019 | Nelson | G16H 50/80 |
| | | | 703/11 |
| 2019/0307106 A1* | 10/2019 | Hartung | A01K 29/00 |
| 2021/0393658 A1* | 12/2021 | Duval | A23K 50/75 |
| 2022/0039357 A1* | 2/2022 | Roth | G06N 20/00 |

* cited by examiner

ARTIFICIAL INTELLIGENT SYSTEM FOR MANAGING A POULTRY HOUSE

CROSS-REFERENCE TO RELATED APPLICATION

This application claims priority of U.S. Patent Application No. 62/944,949, filed on Dec. 6, 2019.

FIELD

The disclosure relates to an artificial intelligent system for managing a poultry house.

BACKGROUND

The layer industry (e.g., chicken layer industry) is facing multiple challenges in a number of key technical aspects. For example, in conventional chicken poultry houses, monitoring of harmful ambient chemical materials, bacteria and/or viruses, automatic sensing and surveillance of chicken layers, recycling and reuse of chicken excreta as manure, health management of chicken layers, and zoonotic disease prevention are aspects that can potentially be improved. As advancements are made in various technologies (such as artificial intelligence of things (AIoT), which is a combination of artificial intelligence and the Internet of things, big data process including storage, analysis and digitalization of a large amount of data, etc.), it may be beneficial to apply the newly developed technologies in the layer industry.

SUMMARY

Therefore, one object of the disclosure is to provide an artificial intelligence system for use in a poultry house.

According to one embodiment of the disclosure, an artificial intelligence system is for use in a poultry house, and includes:
- a control server;
- a network gateway disposed in the poultry house and equipping with a wireless communication capability;
- a movable sensor module disposed in the poultry house, wherein the movable sensor module is movable within the poultry house for obtaining a plurality of environmental parameters associated with specific locations within the poultry house; and
- a sampling machine disposed in the poultry house for obtaining a sample of poultry waste on the ground of the poultry house.

The movable sensor module is in communication with the network gateway to transmit the environmental parameters to the network gateway, and the network gateway is configured to transmit the environmental parameters to the control server for processing the environmental parameters.

According to one embodiment of the disclosure, an artificial intelligence system is for use in a poultry house, and includes:
- a control server;
- a network gateway disposed in the poultry house and equipping with a wireless communication capability;
- a movable sensor module disposed in the poultry house, wherein the movable sensor module is movable within the poultry house for obtaining a plurality of environmental parameters associated with specific locations within the poultry house; and
- a sampling machine disposed in the poultry house for obtaining a sample of poultry waste on the ground of the poultry house.

The movable sensor module is in communication with the network gateway to transmit the environmental parameters to the network gateway, and the network gateway is configured to transmit the environmental parameters to the control server for processing the environmental parameters.

The system further includes a mass spectrometer disposed in the poultry house.

When it is determined that the environmental parameters are abnormal, the control server controls the sampling machine to obtain the sample of poultry waste at a location of the movable sensor module.

After obtaining the sample of poultry waste, the control server controls the sampling machine to provide the sample of poultry waste to the mass spectrometer for determining whether the sample of poultry waste contains a specific fecal bacteria.

The control server is configured to partition the poultry house into a plurality of sections.

The movable sensor module is configured to obtain the environmental parameters for each of the sections.

The control server is configured to, for each of the sections, obtain a representative parameter based on at least the environmental parameters obtained by the movable sensor module for the section;

the control server is configured to assign one of a plurality of states to each of the sections, the plurality of states including at least a normal state and an abnormal state.

The control server is configured to sort the representative parameters for the sections, to assign a preset number of the sections having the highest representative parameter among all the sections with the abnormal state, and to assign the remaining ones of the sections with the normal state.

According to one embodiment of the disclosure, an artificial intelligence system is for use in a plurality of poultry houses in different geographical regions, and includes, for each of the poultry houses:
- a control server;
- a network gateway disposed in the poultry house and equipping with a wireless communication capability;
- a movable sensor module disposed in the poultry house, wherein the movable sensor module is movable within the poultry house for obtaining a plurality of environmental parameters associated with specific locations within the poultry house; and
- a sampling machine disposed in the poultry house for obtaining a sample of poultry waste on the ground of the poultry house.

The movable sensor module is in communication with the network gateway to transmit the environmental parameters to the network gateway, and the network gateway is configured to transmit the environmental parameters to the control server for processing the environmental parameters.

The system further includes, for each of the poultry houses, a mass spectrometer, a plurality of feeding machineries and a movable conveying machine.

When it is determined that the environmental parameters are abnormal, the control server controls the sampling machine to obtain the sample of poultry waste at a location of the movable sensor module.

After obtaining the sample of poultry waste, the control server controls the sampling machine to provide the sample of poultry waste to the mass spectrometer for determining whether the sample of poultry waste contains a specific fecal bacteria.

When the control server determines that the sample of poultry waste contains a specific fecal bacteria, the control server controls the movable conveying machine to provide a medicine to one of the feeding machineries that corresponds to the location of the movable sensor module.

The system includes a plurality of the movable sensor modules, each for a respective one of the poultry houses. For each of the poultry houses, the movable sensor module is configured to obtain the environmental parameters for the poultry house.

The control server is configured to, for each of the poultry houses, obtain a representative parameter based on at least the environmental parameters obtained by the movable sensor module for the poultry house.

The control server is configured to sort the representative parameters for the poultry houses, to assign a preset number of poultry houses having the highest representative parameter with the abnormal state, and to assign the remaining ones of the poultry houses with the normal state.

The control server is further configured to determine, based on at least the spatial distribution of the poultry houses with the abnormal state, whether a disease is spreading among the poultry houses.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
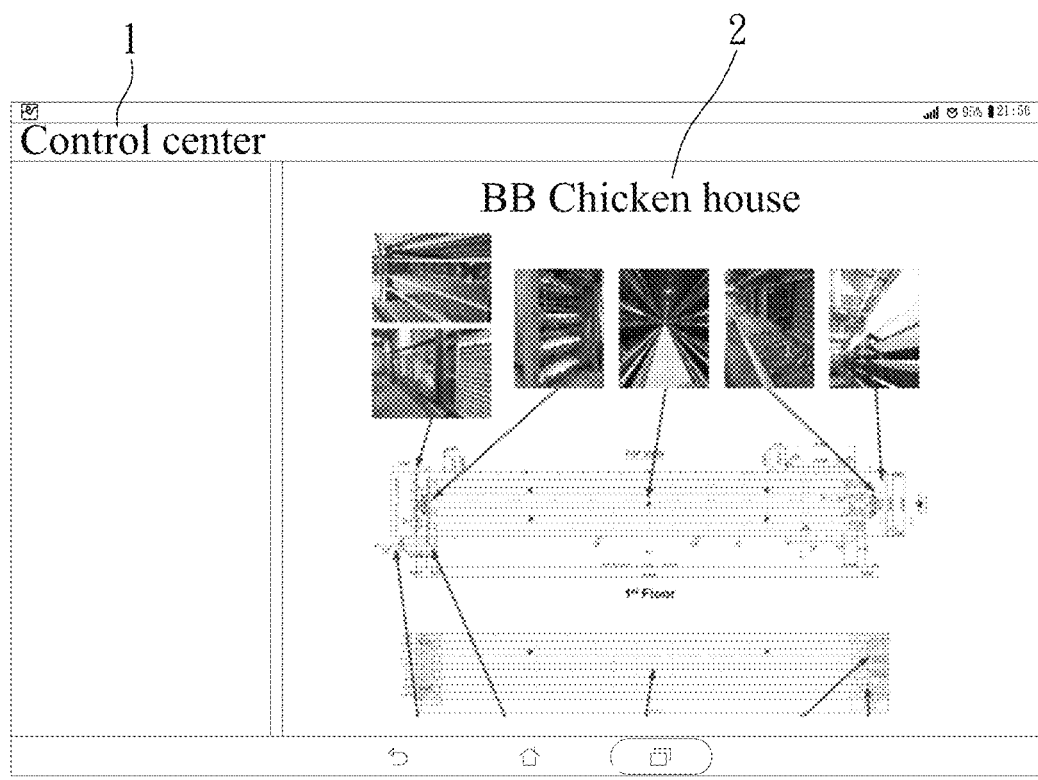
FIGS. 1 and 2 illustrate a poultry house according to one embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

This disclosure provides an intelligent system for managing a poultry house, for example, to enhance production of eggs. Specifically, the intelligent system implements various functions such as smart layer production and management, monitoring of harmful substances and bacteria, monitoring of layer health indices, zoonotic disease prevention and health improvement in layers. The implementation of the above functions may be done using AIoT, big data management and digitalization. The resulting artificial intelligence system for layer production may be configured to function alone or in combination with existing automated equipments.

Functions that are covered by the artificial intelligence system of the disclosure include, but not limited to, the following: 1) sampling, sensing and monitoring of harmful substances and zoonotic bacteria in-poultry houses; 2) automatic sensing and surveillance conducted for physiological research and study and monitoring of egg production in layers; 3) application of intelligent remote control and Internet of things in layers; and 4) big data storage, analysis and digitalization.

Figure 2:
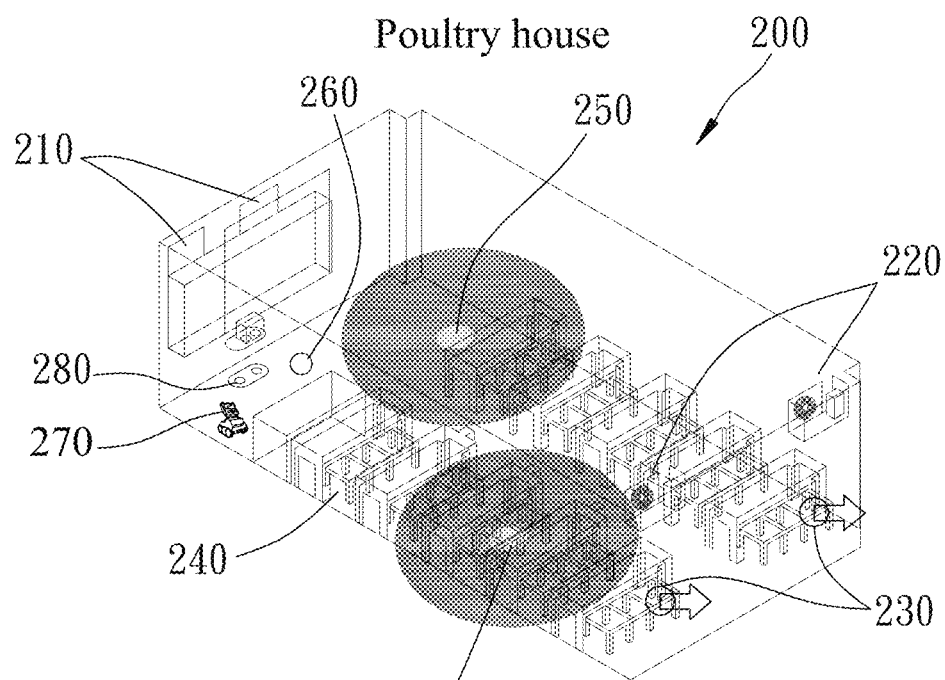

FIGS. 1 and 2 illustrate a poultry house 200 according to one embodiment of the disclosure. In this embodiment, the poultry house 200 is a chicken house that is configured for housing, for example, laying hens (also known as layers) that lay eggs. The poultry house 200 may be equipped with one or more windows 210, one or more air conditioning devices 220, one or more exhaust fans 230, one or more feeding machineries 240, at least one network gateway 250, at least one movable sensor module 260, a sampling machine 270, and a mass spectrometer 280.

Figure 6:
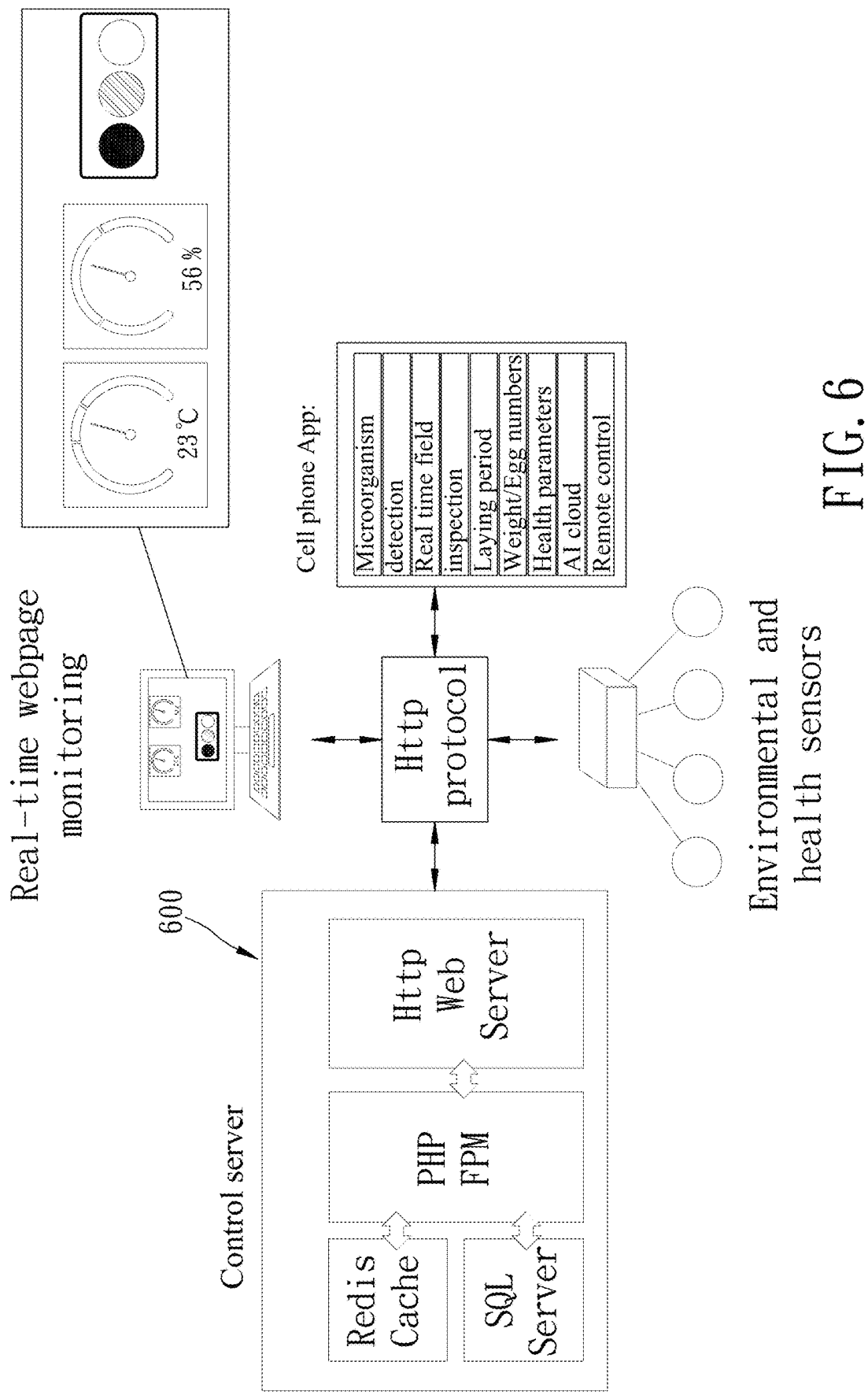
FIG. 6 is an exemplary graph illustrating a network gateway 250 communicating with a control server 600, a monitor screen and a mobile device through a communication network.

It is noted that each of the above-mentioned components placed in the poultry house 200 may be equipped with a microprocessor and a Bluetooth® 5.0 (BT-5.0) equipment, so as to be able to communicate with the network gateway 250. Additionally, the network gateway 250 is configured to communicate with a control server 600 through a communication network (see FIG. 6). The control server 600 may be embodied using a remote server (e.g., a cloud server) disposed outside of the poultry house 200 and communicating with the network gateway 250 through the Internet, or a micro server disposed in the poultry house 200 and communicating with the network gateway 250 through near-field communication network.

In consideration of the possible communication range of the BT-5.0 protocol (approximately 400 meters), a large number of components equipped with the Bluetooth® 5.0 communication capability within the poultry house 200 may communicate with one another. In this embodiment, around two-thousand components may be implemented in the poultry house 200.

In this configuration, operations of the components in the poultry house 200 may be controlled by the control server 600 executing an operating system (OS) that includes a plurality of applications/algorithms, and may be monitored by a user operating an electronic device executing an application.

Specifically, each window may be controlled to open or close. The air conditioning devices 220 may be controlled to keep the temperature inside the poultry house 200 approximately at a predetermined temperature level.

Figure 3:
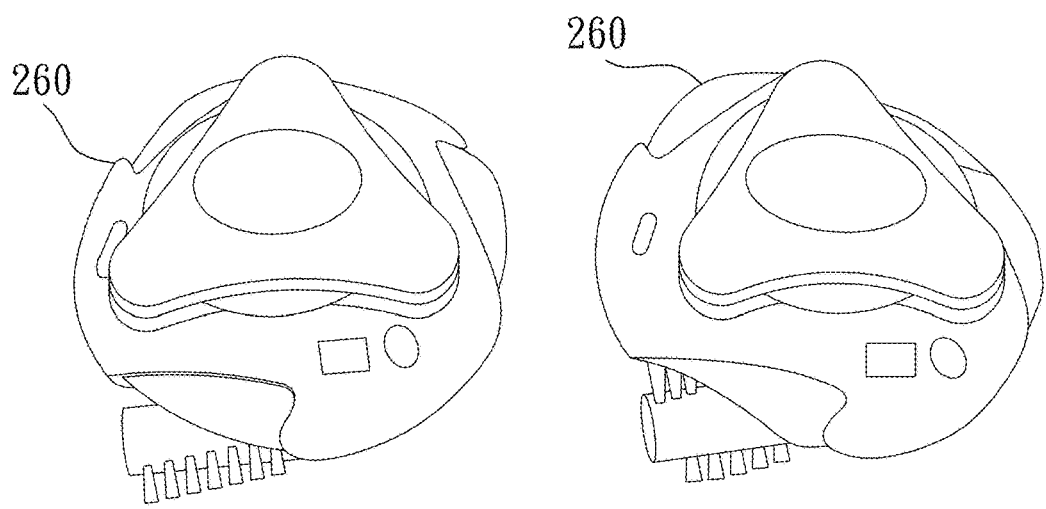
FIG. 3 is a schematic view of a movable sensor module.

As shown in FIG. 3, the movable sensor module 260 is configured for sensing environmental parameters at different places in the poultry house 200, and may include various sensors (e.g., a thermometer, a hygrometer, a carbon dioxide sensor, etc.). The environmental parameters may include a temperature, a relative humidity (Rh), concentrations of specific gas substances (e.g., ammonia, carbon dioxide, etc.). It is known that the temperature in the poultry house 200 may directly affect egg production. The concentration of ammonia gas can be considered as a health index of the layers in the poultry house 200 since the ammonia gas is expelled from the cloaca of the layers.

In this embodiment, the sensors are disposed on a main body of the movable sensor module 260, and the main body is disposed on a wheel set (one example shown in FIG. 4A) that includes at least one wheel. The wheel set may be controlled by a microprocessor executing an application, so as to drive the main body to move within the poultry house 200. In other embodiments, the sensors may be disposed in a ball-shaped outer shell (one example shown in FIG. 4B) of the movable sensor module 260, which may be actuated to roll so as to move the sensor components within the poultry house 200. In some embodiments, the poultry house 200 may be installed with one or more slide tracks (one example shown in FIG. 4C) that extend within the poultry house 200, and the movable sensor module 260 may be disposed on the slide tracks to move thereon.

In such a manner, it is made possible for the movable sensor module 260 to obtain data of the environmental parameters at various locations in the poultry house 200, and to transmit the data of the environmental parameters to the control server 600. In some embodiments, the movable sensor module 260 is provided with on-device AI (artificial intelligence) so that the movable sensor module 260 can process the data of the environmental parameters obtained thereby.

Figure 5:
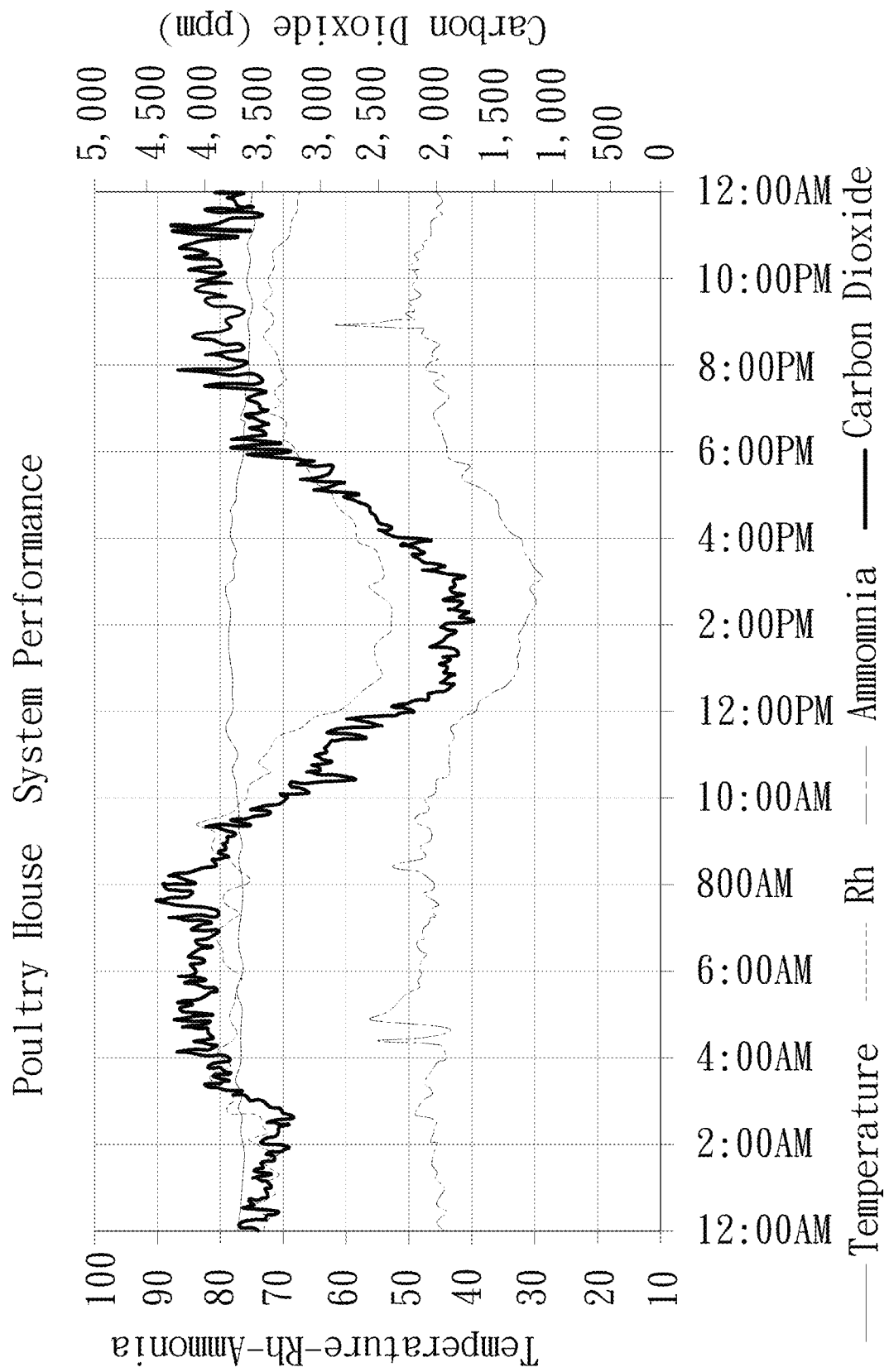
FIG. 5 is an exemplary graph illustrating the statistics from the data obtained throughout a day.

The control server 600 may then process the data of the environmental parameters to derive statistics related to the environment of the poultry house 200, the health of the layers, etc., from the data. For example, as shown in FIG. 5, the statistics from the data obtained throughout a day may be displayed using a graph for further analysis (e.g., to identify a high/low point, a trend, etc.).

A number of advantages are achieved by using the movable sensor module 260 to monitor the environmental parameters at different locations in the poultry house 200. For example, the poultry house 200 typically accommodates a large number of laying hens, and due to the different health aspects/conditions of the laying hens, a detected value of each of the environmental parameters may be different for the different locations of the poultry house 200 (for example, different body temperatures of the laying hens may affect the environmental temperature in the poultry house 200). As a result, using a single stationary sensor installed at a fixed location in the poultry house 200 to monitor of the environment of the poultry house 200 may not yield an accurate result that is representative of the dynamic situation of the poultry house 200.

Additionally, it is beneficial to monitor the environmental parameters in the poultry house 200 since it is desirable to keep the environment of the poultry house 200 stable, since deviating from a predetermined optimal condition (for example, a one-degree increase/decrease in the temperature) may have an adverse effect on the egg production. Therefore, by using the movable sensor module 260 to monitor the environmental parameters at varying locations in the poultry house 200, deviation of the environmental parameters from the predetermined optimal condition at different locations in the poultry house 200 may be easier to detect.

Since the movable sensor module 260 is in communication with the network gateway 250, data regarding the environmental parameters detected by the movable sensor module 260 may be transmitted to the network gateway 250 in real time. In turn, the network gateway 250 may transmit the data regarding the environmental parameters to the control server 600. As such, the control server 600 may process the data to determine whether the poultry house 200 is in an optimized state. It is noted that in some embodiments, the processing of the data may be done by the microprocessor of the network gateway 250 or by the movable sensor module 260 (on-device AI).

When it is determined that an abnormality has been detected with the help of the movable sensor module 260 (e.g., as indicated in the values of the detected environmental parameters, such as a relatively higher temperature, a higher concentration of ammonia than a preset standard, etc.) at a location in the poultry house 200, the control server 600 may determine that the health of the laying hens situated within a detected area near the corresponding location of the movable sensor module 260 in the poultry house 200 at the time of the detection may require inspection. Subsequently, the control server 600 may automatically control the sampling machine 270 to the detected area.

Figure 7:
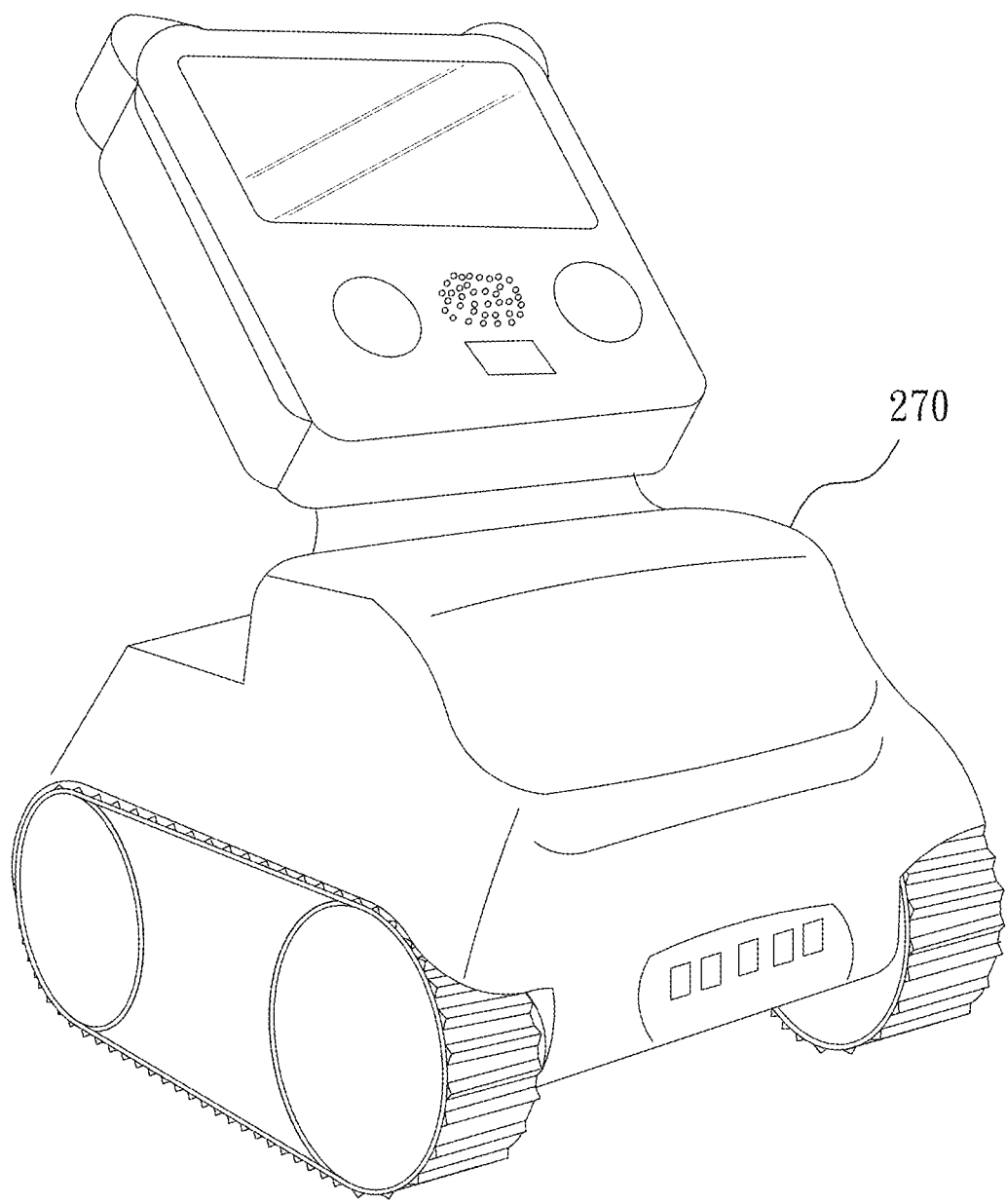
FIG. 7 is an exemplary graph illustrating a sampling machine.

As shown in FIG. 7, the sampling machine 270 may include a continuous track, and can be controlled to move to specific locations in the poultry house 200. In one example, the sampling machine 270 may be controlled to move to the detected area mentioned above. When the sampling machine 270 moves to the detected area, a set of robotic arms of the sampling machine 270 may be utilized to obtain a sample of poultry waste on the ground of the detected area.

Figure 8:
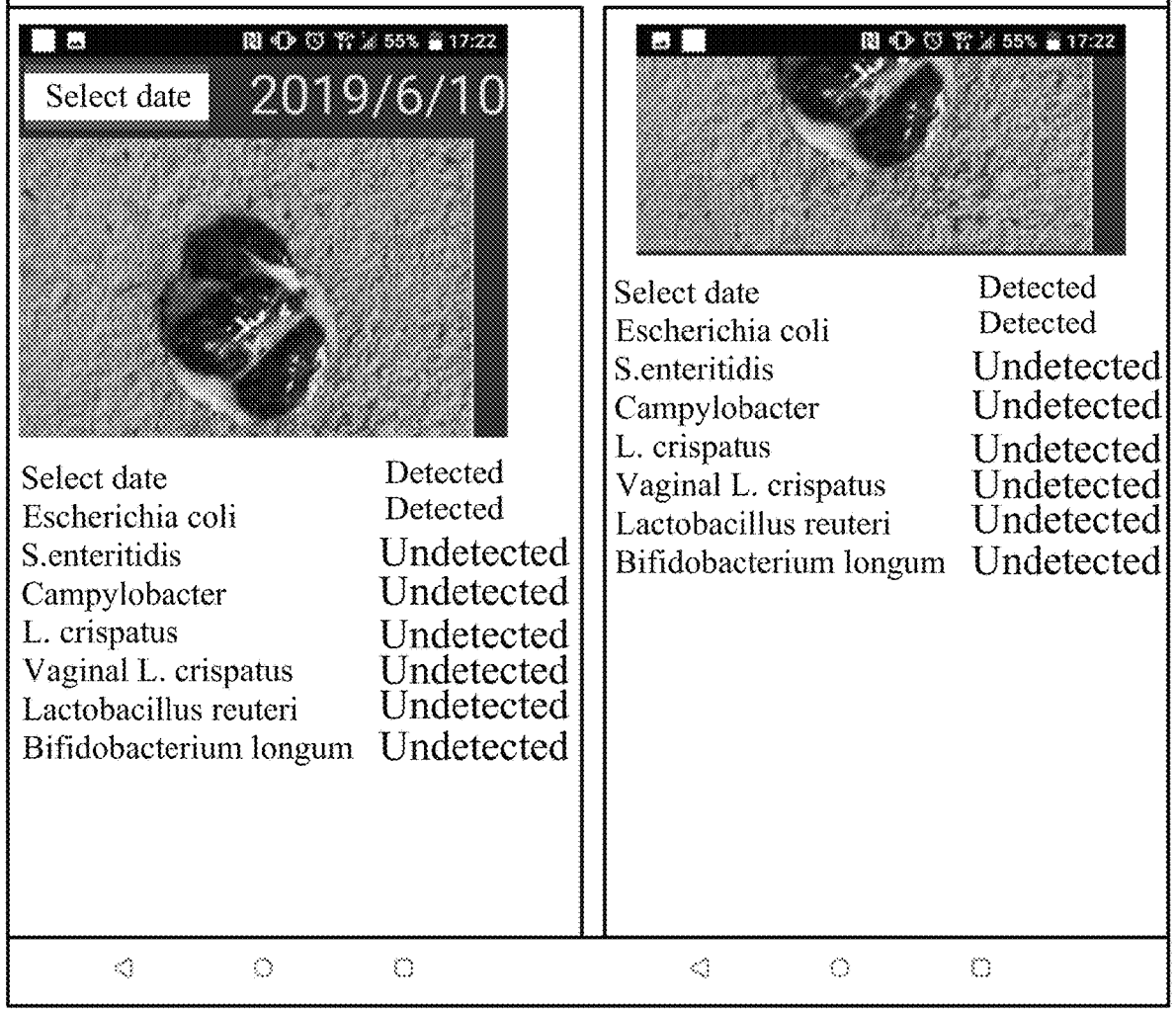
FIG. 8 illustrates a result of the detection for specific fecal bacteria by a mass spectrometer.

Then, the sampling machine 270 may be controlled to move to a location where the mass spectrometer 280 is located, so as to provide the sample of poultry waste to the mass spectrometer 280 for further inspection. The mass spectrometer 280 may be configured to detect several species of fecal bacteria, so as to determine whether the laying hens in the detected area are afflicted with a disease. A result of the detection for specific fecal bacteria may be displayed in a manner as shown in FIG. 8.

Figure 4A:
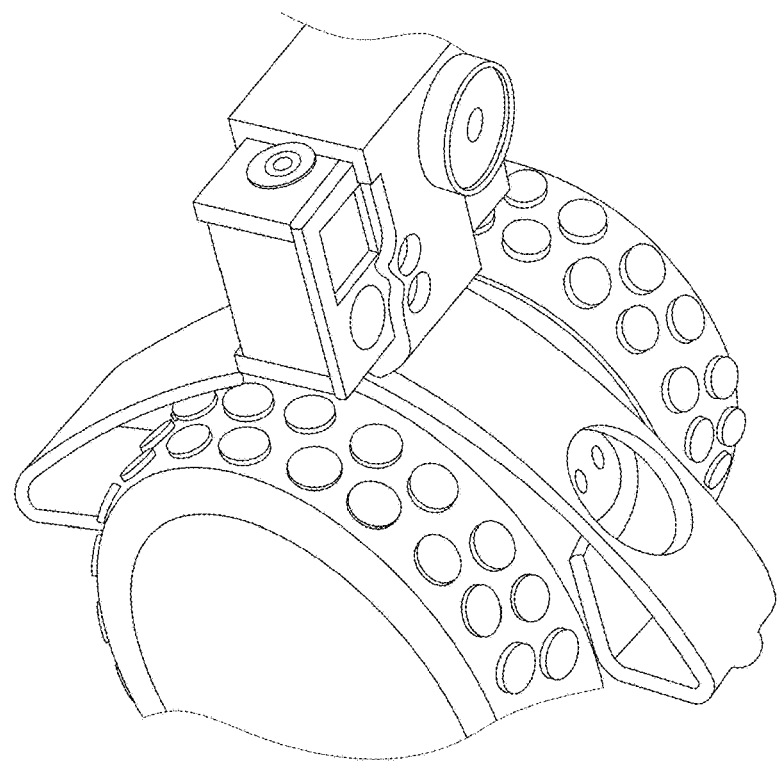
FIGS. 4A to 4C illustrate a number of exemplary mechanisms for enabling the movable sensor module to move.
Figure 4B:
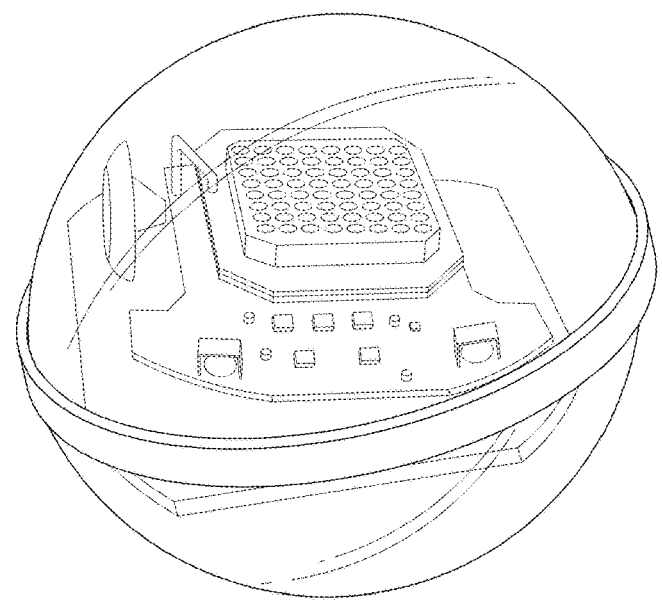
Figure 4C:
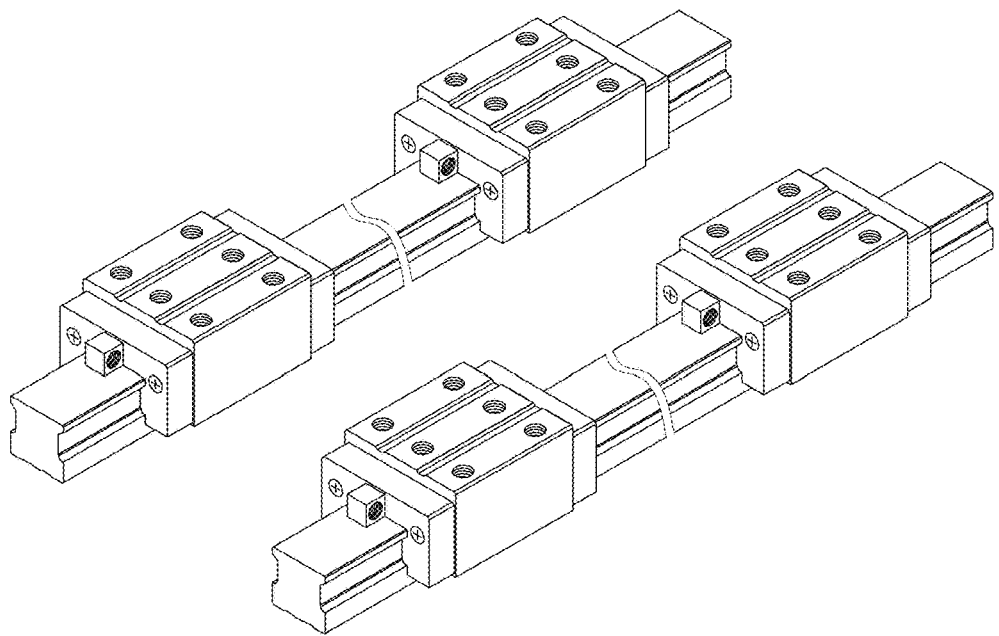

In one embodiment, after it is determined that the laying hens in the detected area might be afflicted with a disease, the control server 600 may control a movable conveying machine to administer medicine (e.g., probiotics) that is used to treat the disease to one or more of feeding machineries 240 that are located in the detected area. The conveying machine may be integrated with the feeding machineries 240 (therefore not depicted in the drawings) or may be embodied in a same manner as the movable sensor module 260; that is, the conveying machine may include a track belt or a wheel set so as to move within the poultry house 200 (as seen in FIGS. 4A to 4C). Additionally, the control server 600 may generate an alert (e.g., a push message, a text message, an audible sound, etc.) to notify a personnel of the situation. In some embodiments, the conveying machine may be omitted, and an automated supplying mechanism may be disposed above a feed tray that contains feed for the laying hens. The supplying mechanism contains the medicine for treating the disease, and can be controlled to supply the medicine to the feed tray.

In brief, the configuration of the intelligent system is made to implement an artificial intelligence of things (AIoT) in the poultry house 200, and is capable of performing operations such as detecting the environmental parameters at different locations of the poultry house 200, processing the data of the environmental parameters detected in real time, sampling the poultry waste in detected area(s) with abnormal environmental parameters detected, and moving the sample of poultry waste to the mass spectrometer 280 for inspection, so as to immediately determine whether the laying hens in the detected area are afflicted with a disease. By implementing the AIoT, all the above operations may be done automatically by the control server 600 controlling the components.

Each feeding machinery 240 may be connected to a feed storage that stores feed therein, and is configured to transport the feed from the feed storage to one or more locations in the poultry house 200 via a number of transmitting tubes and openings that can be controlled to open (to start releasing the feed) or to close (to stop releasing the feed).

Figure 9:
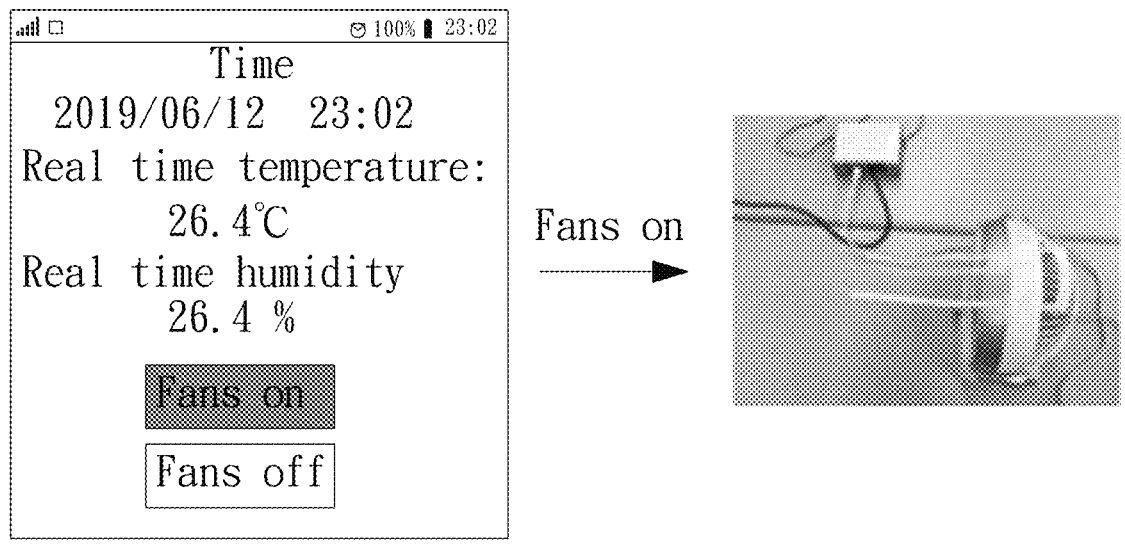
FIG. 9 illustrates an interface on a mobile device to transmit a signal to control one or more exhaust fan(s) to turn on or to turn off.
Figure 9:
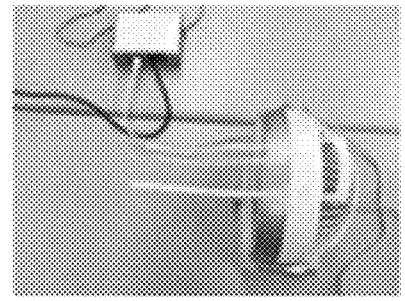
Figure 9:
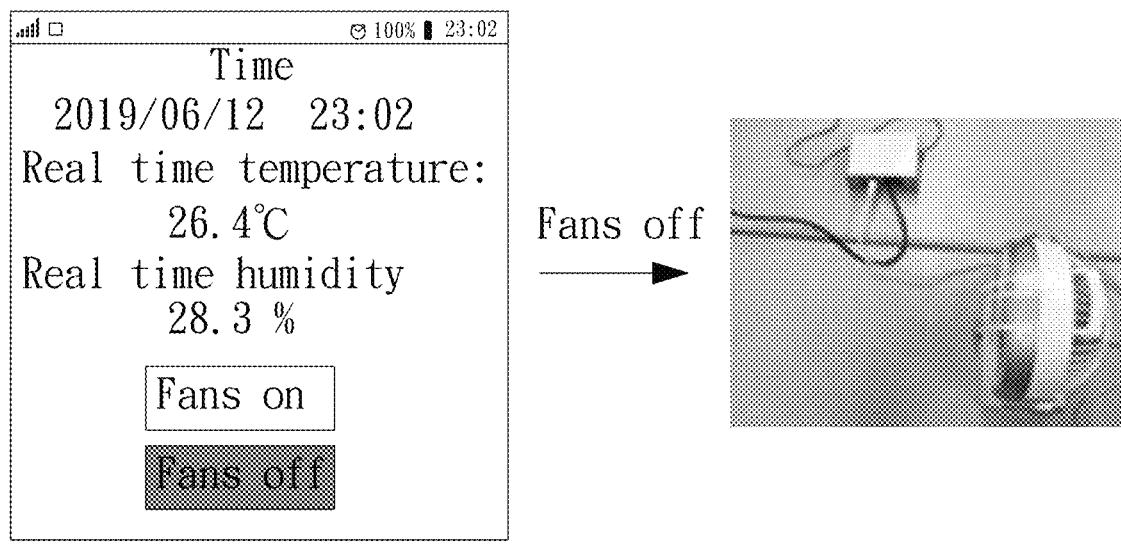
Figure 9:
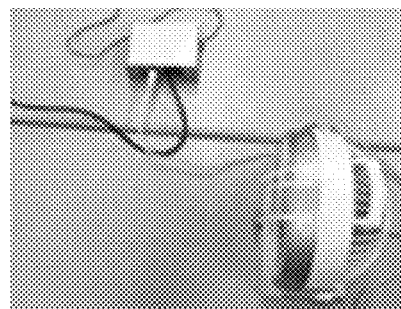

In one embodiment, operations of the components of the poultry house 200 may be different in response to different detected values of the environmental parameters. For example, the exhaust fans 230 may be individually or altogether controlled to turn on or turn off based on a detected temperature within an area, a detected temperature outside the poultry house 200, and/or a general temperature of the geographical area where the poultry house 200 is located. To be specific, when a difference between the detected temperature of the area and the detected temperature outside the poultry house 200 is greater than a predetermined threshold, the exhaust fans 230 are turned on to adjust the temperature in the poultry house 200. One or more of the air conditioning devices 220 may be controlled to operate based on one or more of the following parameters: the detected temperature in the poultry house 200, a detected humidity, a detected concentration of harmful gas substances, etc. In addition, each of the exhaust fans 230 may also be controlled by personnel operating an electronic device (such as a mobile device, e.g., mobile phone executing an application) that is configured to display the environmental parameters. For example, the environmental parameters may be controlled to be displayed by the mobile device, and based on the environmental parameters, the personnel may operate the mobile device to transmit a signal to control the exhaust fans 230 to turn on or to turn off (as shown in FIG. 9).

It is noted that all the data thus obtained and processed by the control server 600 may be stored in a data storage for further analysis (i.e., big data) by one or more neural networks that constitute an artificial intelligence network. As a number of poultry houses 200 that employ the intelligent system increases, an amount of data gathered may increase as well, facilitating future big data analysis, digitalization, and optimization of the intelligent system.

In some embodiments, a number of stationary sensor modules may be disposed at various locations in the poultry house 200. The number and location of the stationary sensor modules may be determined based on an effective range of the stationary sensor modules.

In some embodiments, inside the inner space of the poultry house 200, there are a plurality of cages for housing the laying hens.

In some embodiments, the inner space of the poultry house 200 may be partitioned into multiple virtual sections. That is to say, no physical boundary is present. The virtual sections may be defined based on coverage of the stationary sensor modules. In other embodiments, the inner space of the poultry house 200 may be partitioned into multiple virtual sections based on a three-dimensional coordinate system, and each virtual section is defined by a set of three-dimensional coordinates of the three-dimensional coordinate system. Each of the virtual sections may be covered by the effective range of one of the stationary sensor modules, or covered by one or more of the movable sensor modules 260. In other examples, the control server 600 may designate an area of one cage as a virtual section, or designate an area of a predetermined number of cages (e.g., two or three) to serve as a virtual section. In each of the virtual sections, one stationary sensor module may be installed for detecting the environmental parameters within the virtual section.

As such, for each of the virtual sections, one of a plurality of "states" may be assigned to indicate whether the environment of the virtual section is normal or whether the environment of the virtual section is abnormal and may require treatment (such as providing medicine). The state of the virtual section is assigned by the control server 600 based on one or more of the environmental parameters (e.g., temperature) detected within the virtual section.

Figure 10:
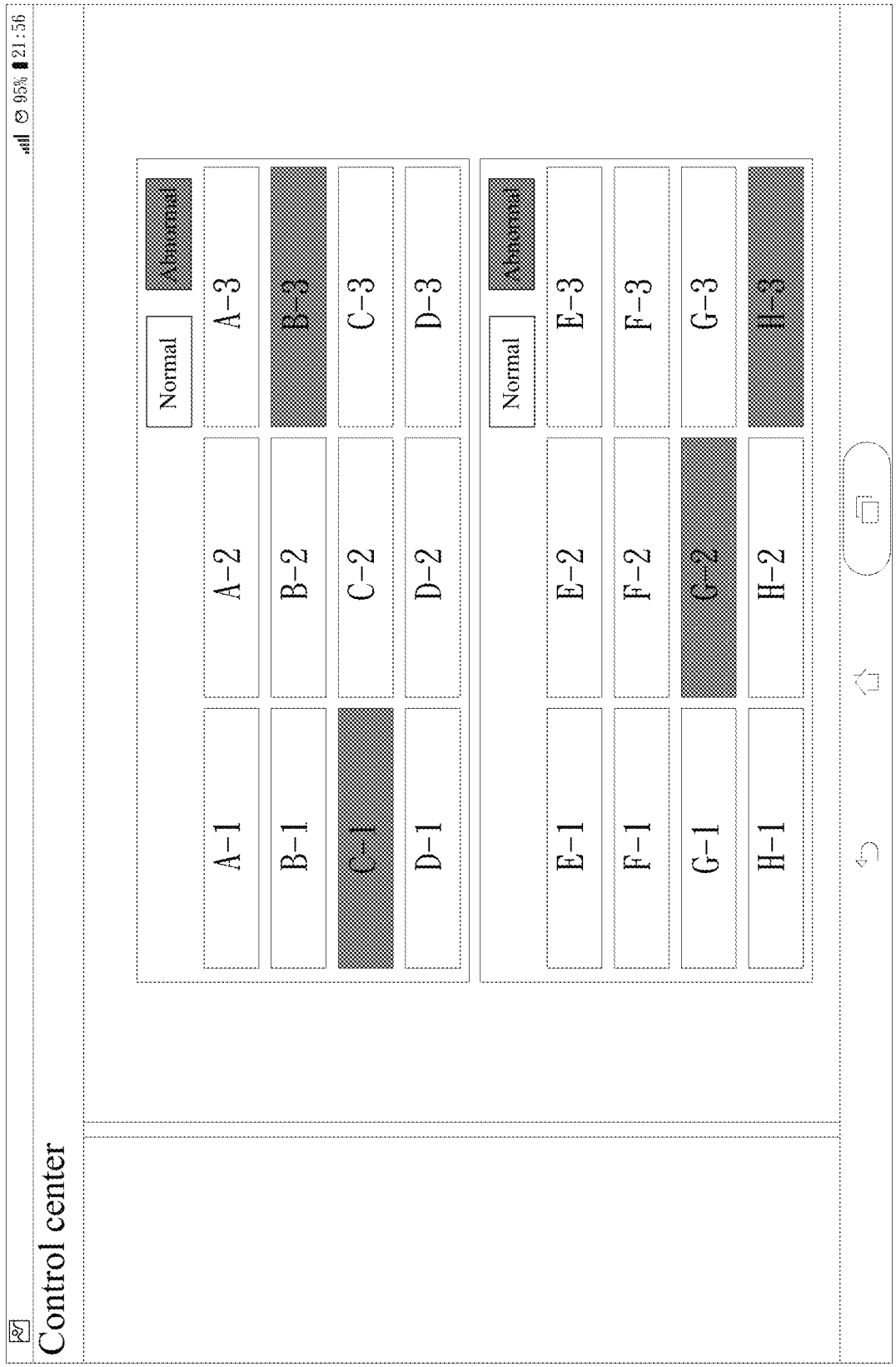
FIG. 10 illustrates a display screen displaying conditions of a number of virtual sections of the poultry house.

In one embodiment, the poultry house 200 has two floors, each being partitioned into twelve virtual sections. When the environmental parameters detected in each of the virtual sections are transmitted to the control server 600, the control server 600 may determine, for each of the virtual sections, whether the virtual section is in a "normal" state or an "abnormal" state. As shown in FIG. 10, each of the first and second floors of the poultry house 200 is divided into twelve virtual sections, the virtual sections that are deemed to be in the normal state may be represented using one color (e.g., green), and the virtual sections that are deemed to be in the abnormal state (referred to as abnormal sections) may be represented using another color (e.g., red). It is noted that in some embodiments, additional states may be assigned to indicate various environmental conditions of the virtual sections, and may be represented using other colors (e.g., yellow). In this manner, the health conditions for all virtual sections may be displayed on a screen in different colors to be visually perceivable by the personnel.

In one embodiment, an effective temperature (e.g., an average over a time period) of each of the twenty-four virtual sections is collected, and the twenty-four effective temperatures are sorted to determine a preset number (for example, four) of the highest effective temperatures. Subsequently, four of the virtual sections having the four highest effective temperatures are assigned the abnormal state, while each of the remaining virtual sections is assigned with the "normal" state. In other embodiments, other environmental parameters (e.g., a concentration of ammonia) may be included in the calculation to obtain a representative parameter for each of the twenty-four virtual sections, and the preset number of the virtual sections may be determined to be assigned with the abnormal state based on the representative parameters of the sections. For example, each of the environmental parameters may carry a predetermined weight, and calculating the representative parameter may include calculating a weighted average number from the environmental parameters to serve as the representative parameter.

Using this configuration, the control server 600 may further determine whether a disease, indicated by the abnormal state, is spreading among the poultry house 200 according to distribution of the virtual sections that are assigned with the abnormal state.

Specifically, in one example as shown in FIG. 10, the four virtual sections (i.e., B-3, C-1, G-2 and H-3) having the highest effective temperatures may be deemed to be distributed spatially among the poultry house 200 in a random manner (i.e., no particular pattern and no adjacent abnormal sections are present). Such a determination may also take into consideration the environmental parameters of other virtual sections (for example, location of the virtual section having a fifth highest effective temperature), and/or a rate of change of the environmental parameters.

On the other hand, when the four virtual sections having the highest effective temperatures are in proximity of one another (e.g., all adjacent), it may be deemed that the situation in those virtual sections needs special attention. In such a case, the control server 600 may assign a first level of alert to the poultry house 200, indicating that a disease may be in an initial stage of outbreak within the poultry house 200.

In this stage, the control server 600 may implement a control protocol that includes providing medicine to the laying hens accommodated in the abnormal sections and optionally those other virtual sections that are adjacent to the abnormal sections (referred to as adjacent sections), and sanitizing the environment of the abnormal sections and, optionally, also the adjacent sections. It is noted that in embodiments, the medicine may be provided via the feeding machineries 240.

In addition, in subsequent monitoring of the poultry house 200, the preset number to assign the abnormal sections may be increased (e.g., to six).

Afterward, the monitoring is conducted to determine whether the situation is under control (e.g., the spatial distribution of the abnormal sections becomes "random") or is worsening (e.g., the distribution of the abnormal sections is clustered and spreading or the environmental parameters of the abnormal sections are indicating a worse environmental state) within a predetermined period after, for example, implementing the control protocol for the initial stage of outbreak.

When it is determined that the situation is worsening, the control server 600 may assign a second level of alert to the poultry house 200, indicating that a disease may be in a middle stage of outbreak within the poultry house 200.

In this stage, the control server 600 may implement a stronger control protocol that includes providing medicine to the laying hens accommodated in the abnormal sections and the adjacent sections, and stronger sanitization of the entire environment of the poultry house 200. In addition, in subsequent monitoring of the layer breeding section, the preset number to assign the abnormal sections may be further increased (e.g., to ten).

Afterward, the monitoring is conducted to determine whether the situation is under control (e.g., the distribution of the abnormal sections becomes random) or is still worsening (e.g., the distribution of the abnormal sections is similarly clustered and spreading or the environmental parameters of the abnormal sections are indicating a worse environmental state) within a predetermined period after, for example, implementing the stronger control protocol for the middle stage of outbreak.

When it is determined that the situation is worsening, the control server 600 may assign a third level of alert to the poultry house 200, indicating that a disease may be in an advanced stage of outbreak within the poultry house 200.

In this stage, the control server 600 may implement an even stronger control protocol that includes providing medicine to the laying hens accommodated in all the virtual sections, and sanitizing the entire environment of the poultry house 200. In addition, according to the provisions of specific countries, the control server 600 may generate an alert to notify the personnel of the situation and/or designated government officials of the situation, and the government officials may authorize measures such as culling the livestock in the poultry house 200. In some embodiments, the data in the control server 600 may be accessible to some statutory institutions (e.g., Department of Health) such that the statutory institutions may take precautionary measures (e.g., sending supplies or manpower to assist in the sanitation) or implement the culling.

In one embodiment, for each of the virtual sections in the poultry house 200, a number of sentinels may be designated. The term "sentinel" may be referred to as a laying hen selected to have a detecting equipment mounted thereon, so as to obtain one or more health parameters of the laying hens, which may be representative of laying hens in the same virtual section, or the virtual section itself.

Figure 11:
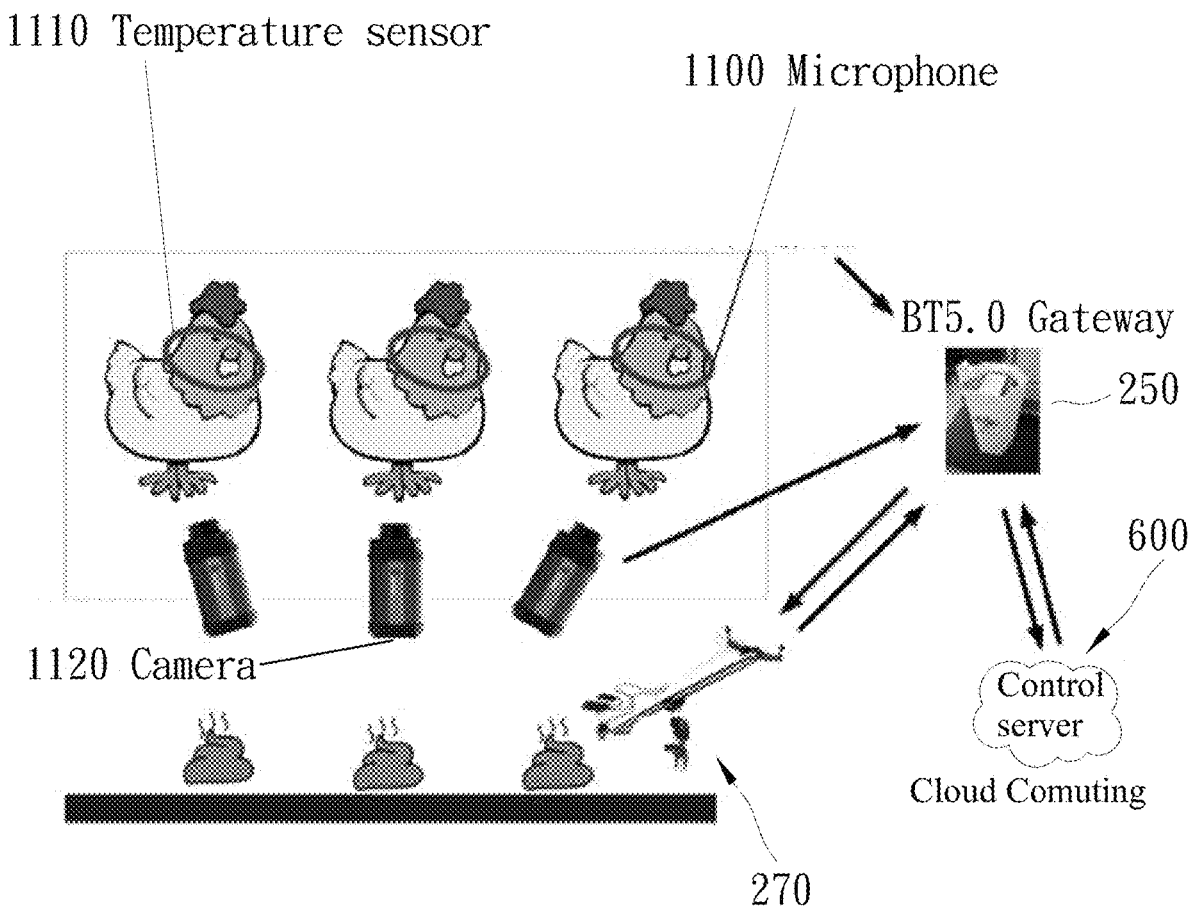
FIG. 11 illustrates a number of the sentinels equipped with a microphone for obtaining voiceprint data of the sentinel, a and a camera for obtaining an image of a cloaca of the sentinel.
Figure 12:
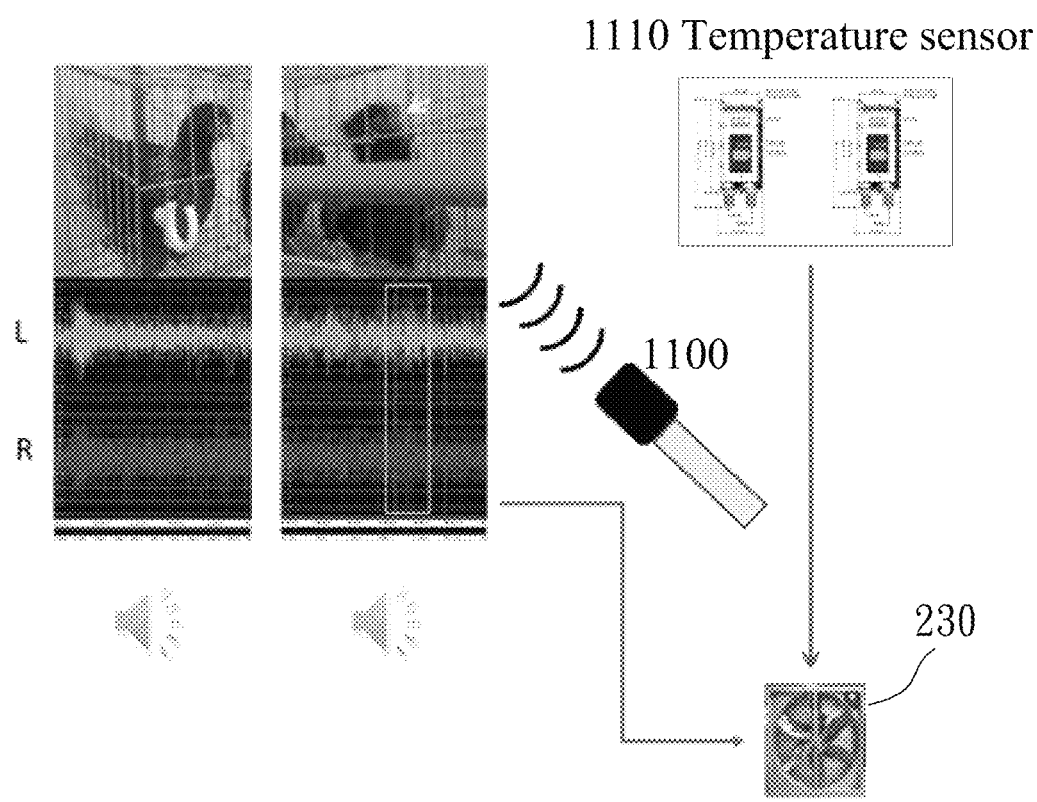
FIG. 12 illustrates using the voiceprint data of the sentinel for controlling one or more exhaust fan(s) to turn on or to turn off.

As shown in FIGS. 11 and 12, in this embodiment, each of the sentinels may be equipped with a microphone 1100 for obtaining voiceprint data of the sentinel, a temperature sensor 1110 for obtaining a body temperature of the sentinel, and a camera 1120 for obtaining an image of a cloaca of the sentinel. It is noted that in some embodiments, the temperature sensor 1110 may be equipped in the poultry house 200 for detecting the temperature in the poultry house 200, and for enabling estimation of the body temperature of the sentinel.

Figure 13:
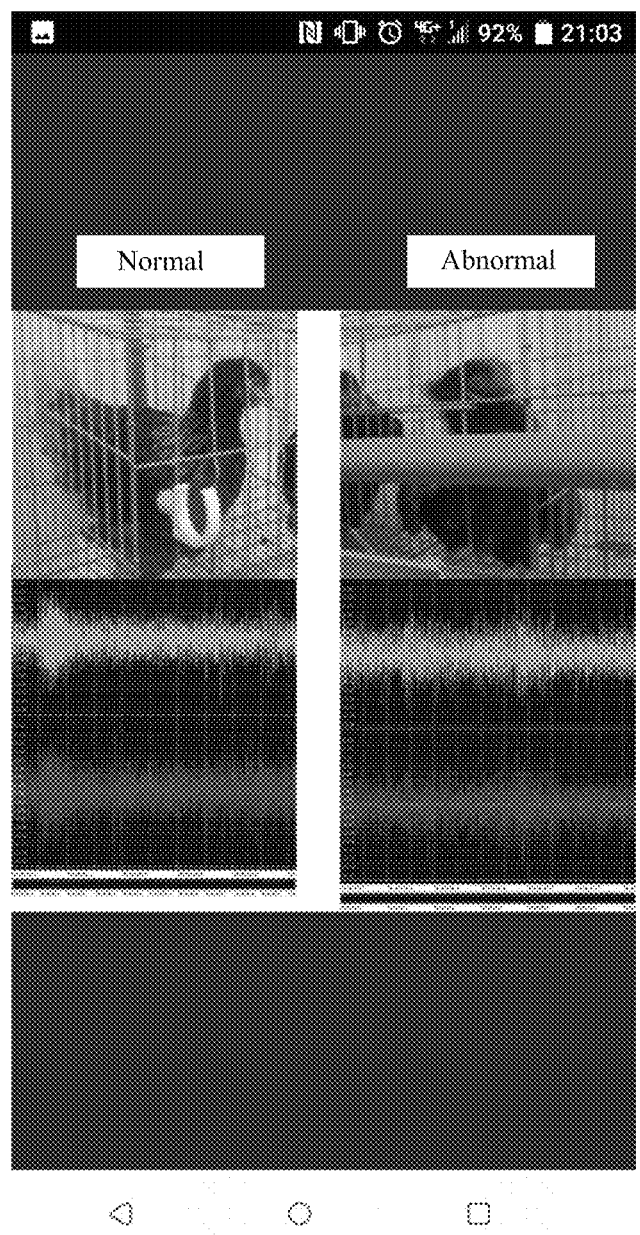
FIG. 13 illustrates voiceprint data of a healthy sentinel (left part) and an unhealthy sentinel (right part)

Processing the voiceprint data of the sentinel may assist in determining whether the sentinel is healthy. For example, as shown in FIG. 13, the voiceprint data of a healthy sentinel may have waveforms as shown in the left part of FIG. 13, while the voiceprint data of an unhealthy sentinel (e.g., one suffering from discomfort in the nasal cavity) may have waveforms as shown in the right part of FIG. 13. Similarly, the body temperature of the sentinel may indicate a health state of the sentinel. By observing the image of the cloaca of the sentinel, the control server 600 may be able to determine whether specific fecal bacteria is present (by, for example, identifying certain colors in the image), and when it is determined that the specific fecal bacteria is present, the control server 600 may implement the sampling machine 270 to obtain a sample of poultry waste for processing, as described above. Using the above data, the health parameter(s) such as a comfort scale of nasal cavity, a health scale of cloaca may be calculated.

Additionally, data collected from a sentinel may be stored as template data. As more data is being collected, the template data may be used for comparison (e.g., comparing the voiceprint data to determine whether another laying hen has discomfort in the nasal cavity) to, for example, facilitate detection of unhealthy hens.

It is noted that the health parameters for the sentinels may be used along with the above environmental parameters for determining the representative parameters of the virtual sections, and for determining the states of the virtual sections (i.e., the normal state or the abnormal state). In addition, the health parameters for the sentinels may be used to determine whether operations of the components in the poultry house 200 need to be adjusted. For example, as shown in FIG. 12, when the voiceprint data of the sentinel indicates that the sentinel is unhealthy, one or more of the exhaust fans 230 may be activated in an attempt to remove airborne contaminants.

Figure 14:
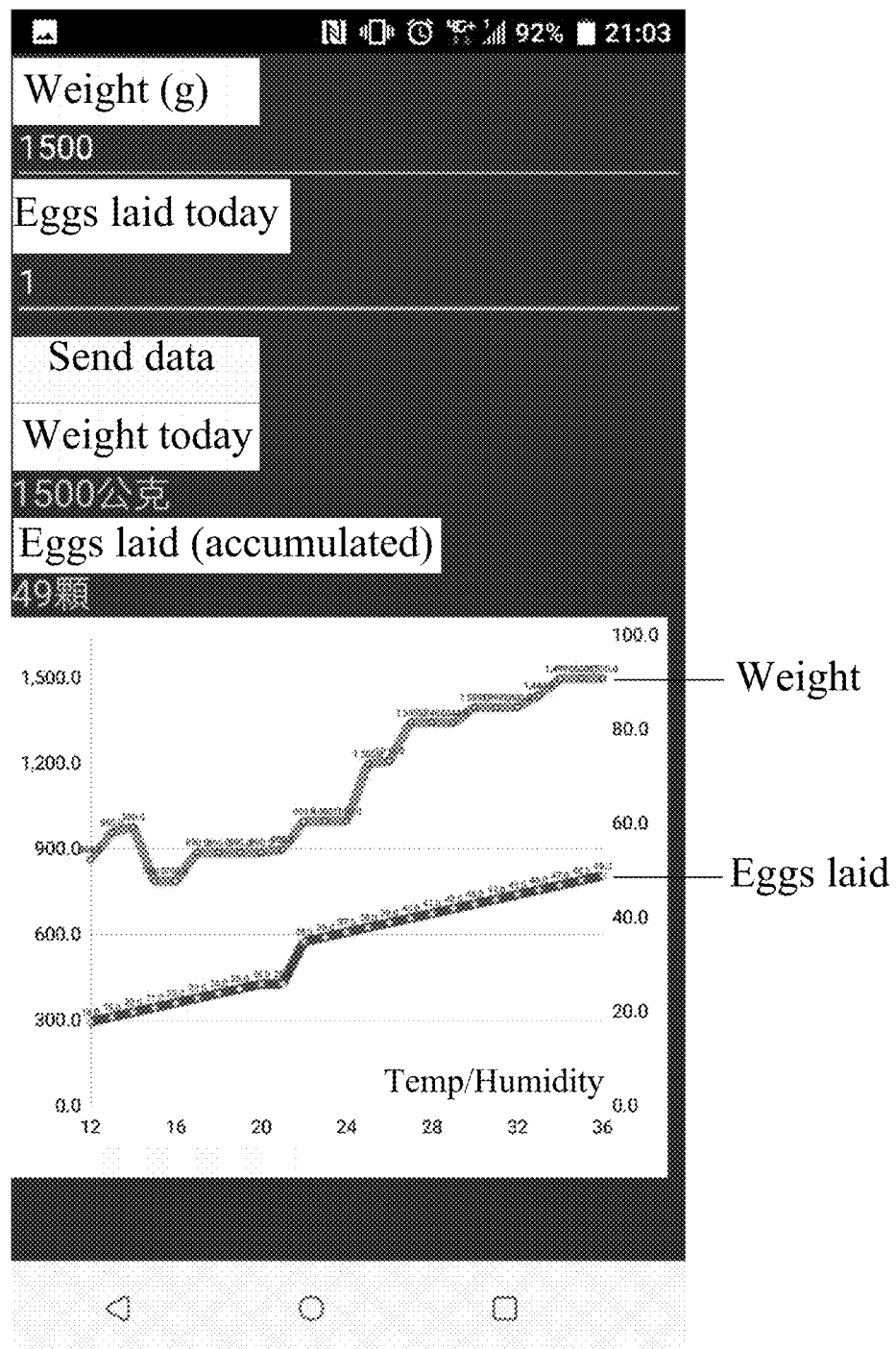
FIG. 14 illustrates an interface for enabling a personnel of the poultry house to input data of other variety regarding the sentinels.

It is noted that data of other variety may also be inputted by the personnel of the poultry house 200 using the mobile device. For example, as shown in FIG. 14, the personnel may manually operate the mobile device to input a weight of the sentinel, a number of eggs laid a day, a photograph of the sentinel, etc. Such data may be processed and displayed using a graph for further analysis (e.g., to identify health trends over a lifetime of the sentinel, to perform a health check, etc.).

Figure 15:
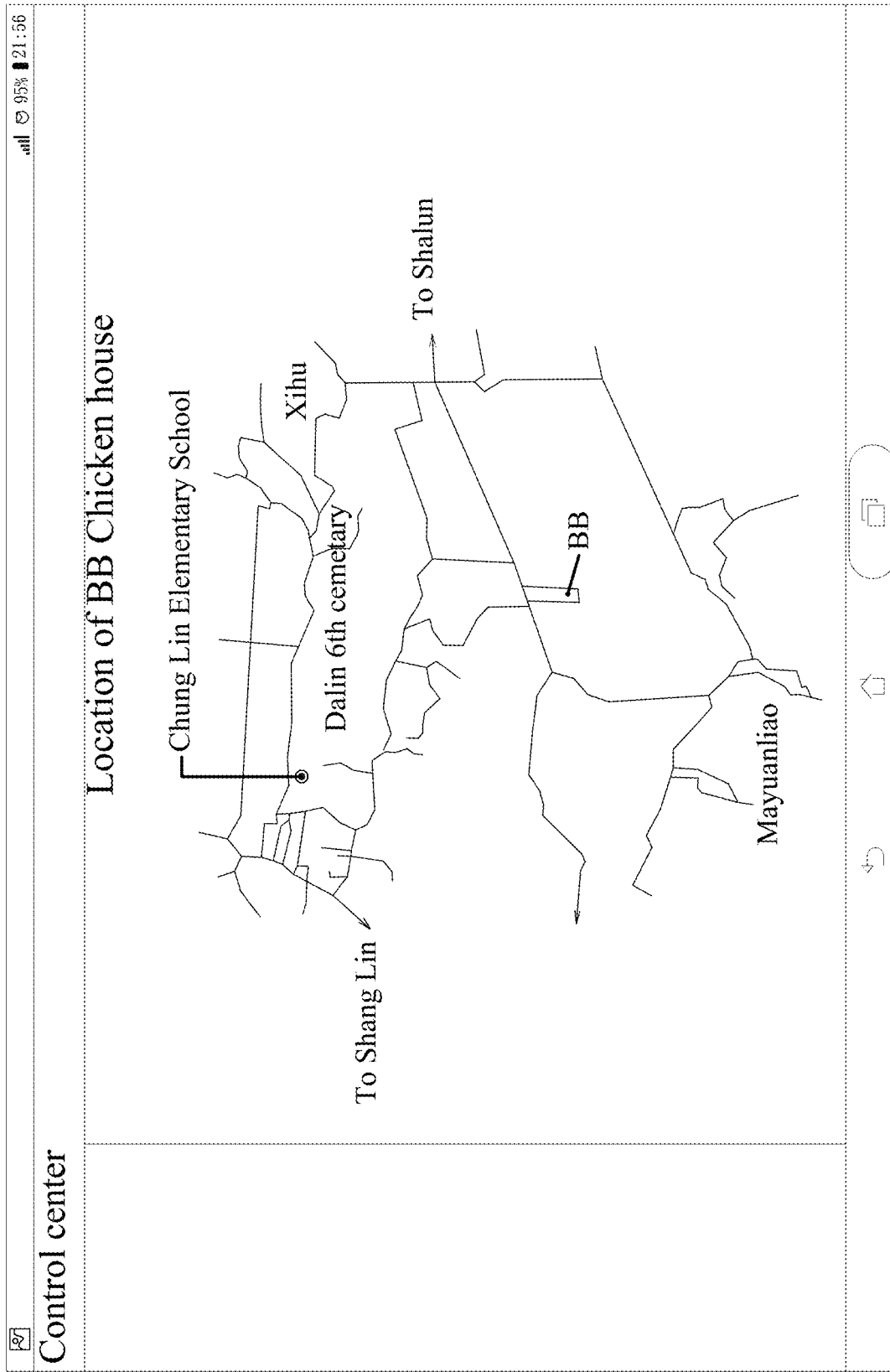
FIG. 15 illustrates an interface for monitoring a number of poultry houses located in different geographical regions.

In one embodiment, the configuration for monitoring a number of virtual sections in one poultry house 200 may be applied to a number of poultry houses 200 located in different geographical regions (as shown in FIG. 15). For each of the poultry houses 200, the health parameters and/or the environmental parameters may be detected and uploaded to the control server 600 (which may be located in a central facility). In such a manner, data related to the number of poultry houses 200 may be displayed in the interface as shown in FIG. 10, and each of the poultry houses 200 may be seen (though of) as a section. The poultry houses 200 that are located relatively closer (e.g., within a distance of 0.5 to 5 kilometers from one another) may be deemed as "adjacent" to one another.

The control server 600 may be configured to assign the abnormal state to a preset number of poultry houses 200. The manner in which the states are assigned may be similar to that as described above, that is, by sorting the values of the representative parameters respectively of the poultry houses 200 in order, and assigning the preset number of the poultry houses 200 with the highest representative parameters as in the abnormal state.

Using this configuration, the control server 600 may determine whether a disease has been spreading among the poultry houses 200 in a manner as described above. That is, the three-level alert mechanism may be employed to determine whether nearby poultry houses 200 are simultaneously being assigned abnormal states, and whether the abnormal states are spreading to other nearby poultry houses 200.

In one example, when one of the poultry houses 200 is deemed to be in the third level of alert, in addition to implementing the above-mentioned measure(s) on the one of the poultry houses 200, the nearby poultry house 200(s) may be alerted so as to get prepared for the potential incoming disease. In such cases, appropriate actions may be taken in order to address the potential disease issue.

It is noted that for each of the poultry houses 200, the personnel may be able to view the interface of FIG. 15 to see not only the poultry house 200 at which the personnel is located, but also other poultry house 200(s) in nearby geographical regions. As such, when one or more poultry houses 200 nearby have the third level of alert, the precautionary measures may also be implemented.

To sum up, the intelligence system as described in the disclosure includes a number of functions and potential effects as follows:

1. Acquisition of health parameter values from a group of sentinels;
2. Collection of environmental parameters for big data analysis;
3. Collection of fecal bacteria for big data analysis;
4. An AI cloud integration platform for monitoring health of the laying hens may be established using the cloud server, the control servers 600 in each of the poultry houses 200, and the components in each of the poultry houses 200;
5. By obtaining relevant data from one or more poultry houses 200 housing a large number of laying hens, further researches in various fields (such as big data analysis, deep learning and AI applications) may be facilitated;
6. Using the above-described system, a tendency of a disease to spread in the group of hens located in one poultry house 200 or among multiple poultry houses 200 may be monitored, based on temporal analyses on the health parameter values or a change in the rate of change of health parameter values;
7. By dividing a poultry house 200 into multiple virtual sections and setting up the stationary sensor modules and/or the movable sensor modules 260, the control server 600 may be able to determine the statuses of sentinels in specific sections within the poultry house 200 (and therefore the statuses of the corresponding groups of the laying hens in said specific sections), which may be displayed on a display using a color to represent the statuses of specific sections within the poultry house 200;
8. By disposing the components that are capable of communicating via the BT-5.0 Gateway, detection of environmental parameters and the health parameters, feeding, and provision of medication may be performed with respect to one or more specific sections within the poultry house 200. As such, an effect of intelligent breeding and "partition isolation" may be achieved; and
9. By assigning a number of laying hens as sentinels, and obtaining the health parameters from the sentinels, evaluation of the health of laying hens may be assisted by further analyzing the health parameters of the sentinels and implementing the three-level protocol, so as to avoid large-scale culling due to disease transmission. Additionally, a database containing health parameters from sentinels of one or more poultry houses 200 may be established, facilitating future analysis. The relevant health data may also be transmitted to nearby poultry houses 200 and/or one or more statutory institutions for alerting the same about the potential spreading of a disease.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. An artificial intelligence system for use in a poultry house, comprising:
   a control server;
   a network gateway disposed in the poultry house and equipped with a wireless communication capability;
   a movable sensor module disposed in the poultry house, wherein said movable sensor module is movable within the poultry house for obtaining a plurality of environmental parameters associated with specific locations within the poultry house; and a sampling machine disposed in the poultry house for obtaining a sample of poultry waste on the ground of the poultry house;

wherein, said movable sensor module is in communication with said network gateway to transmit the environmental parameters to said network gateway, and said network gateway is configured to transmit the environmental parameters to said control server for processing the environmental parameters;

said control server is configured to partition the poultry house into a plurality of sections;

said movable sensor module is configured to obtain the environmental parameters for each of the sections;

said control server is configured to, for each of the sections, obtain a representative parameter based on at least the environmental parameters obtained by said movable sensor module for the section;

said control server is configured to assign one of a plurality of states to each of the sections, the plurality of states including at least a normal state and an abnormal state; and said control server is configured to sort the representative parameters for the sections, to assign a preset number of the sections having a highest representative parameter among all of the sections with the abnormal state, and to assign remaining ones of the sections with the normal state.

2. The system of claim 1, further comprising a mass spectrometer disposed in the poultry house, wherein, when it is determined that the environmental parameters are abnormal, said control server controls said sampling machine to obtain the sample of poultry waste at a location of said movable sensor module;

after obtaining the sample of poultry waste, said control server controls said sampling machine to provide the sample of poultry waste to said mass spectrometer for determining whether the sample of poultry waste contains a specific fecal bacteria.

3. The system of claim 2, further comprising a plurality of feeding machineries and a movable conveying machine;

wherein, when said control server determines that the sample of poultry waste contains a specific fecal bacteria, said control server controls said movable conveying machine to provide a medicine to one of the feeding machineries that corresponds to the location of said movable sensor module.

4. The system of claim 1, wherein said control server is further configured to determine, based on at least the spatial distribution of the sections that are in the abnormal state, whether a disease is spreading within the poultry house.

5. The system of claim 4, wherein when it is determined that a disease is spreading within the poultry house, said control server is further configured to assign a level of alert associated with the poultry house, and to generate a control signal based on the level of alert for performing a control protocol.

6. The system of claim 4, wherein, when the sections with the abnormal state are distributed spatially among the poultry house in a random manner, said control server deems that there is no disease spreading.

7. The system of claim 6, wherein, when it is determined that the sections with the abnormal state are distributed spatially in a particular pattern, said control server is configured to assign a level of alert to the poultry house, and to generate a control signal based on the level of alert for performing a control protocol.

8. The system of claim 7, wherein the control protocol includes at least one of providing medicines, implementing sanitation of one or more of the sections of the poultry house, alerting personnel in a statutory institution, and culling livestock in the poultry house.

9. The system of claim 1, wherein for each of the sections, a sentinel is selected to obtain at least one health parameter, the health parameter being obtained from voiceprint data of the sentinel, a body temperature of the sentinel, and an image of a cloacae of the sentinel.

10. The system of claim 9, wherein said control server is configured to, for each of the sections, obtain a representative parameter further based on the health parameter of the sentinel for the section.

11. The system of claim 9, further comprising a plurality of exhaust fans disposed around the poultry house, each of the sections being associated with at least one of the exhaust fans, wherein, for each of the sections, said control server is configured to, based on the representative parameter for the section, control at least said at least one of the exhaust fans associated with the section to activate or deactivate.

12. The system of claim 1, wherein the poultry house includes a plurality of cages for containing laying hens, and each of the sections is defined to cover at least one cage.

13. The system of claim 12, wherein one stationary sensor module is disposed in each of the sections.

14. The system of claim 1, being for use in a plurality of poultry houses in different geographical regions, wherein:

the system comprises a plurality of said movable sensor modules, each for a respective one of the poultry houses, for each of the poultry houses, said movable sensor module is configured to obtain the environmental parameters for the poultry house;

said control server is configured to, for each of the poultry houses, obtain a representative parameter based on at least the environmental parameters obtained by said movable sensor module for the poultry house.

15. The system of claim 14, wherein said control server is configured to sort the representative parameters for the poultry houses, to assign a preset number of poultry houses having the highest representative parameter with the abnormal state, and to assign the remaining ones of the poultry houses with the normal state.

16. The system of claim 15, wherein said control server is further configured to determine, based on at least the spatial distribution of the poultry houses with the abnormal state, whether a disease is spreading among the poultry houses.

17. The system of claim 16, wherein when it is determined that a disease is spreading among the poultry houses, said control server is further configured to assign a level of alert to the poultry houses, and to generate a control signal based on the level of alert for performing a control protocol.

18. The system of claim 15, wherein, when one of the poultry houses is assigned a level of alert indicating that a disease may be in an advanced stage of outbreak within the poultry house, the control server is configured to further transmit an alert to another of the poultry houses that is in proximity of the one of the poultry houses.

19. The system of claim 1, wherein the wireless communication capability includes at least one of Bluetooth® 5.0 (BT-5.0) capability, 4G capability, or Wi-Fi capability.

20. An artificial intelligence system for use in a poultry house, comprising:
a control server;
a network gateway disposed in the poultry house and equipped with a wireless communication capability;
a movable sensor module disposed in the poultry house, wherein said movable sensor module is movable within the poultry house for obtaining a plurality of environmental parameters associated with specific locations within the poultry house; and
a sampling machine disposed in the poultry house for obtaining a sample of poultry waste on the ground of the poultry house;
wherein said movable sensor module is in communication with said network gateway to transmit the environmental parameters to said network gateway, and said network gateway is configured to transmit the environmental parameters to said control server for processing the environmental parameters;
wherein the system further comprises a mass spectrometer disposed in the poultry house,
wherein, when it is determined that the environmental parameters are abnormal, said control server controls said sampling machine to obtain the sample of poultry waste at a location of said movable sensor module;
after obtaining the sample of poultry waste, said control server controls said sampling machine to provide the sample of poultry waste to said mass spectrometer for determining whether the sample of poultry waste contains a specific fecal bacteria;
wherein said control server is configured to partition the poultry house into a plurality of sections;
said movable sensor module is configured to obtain the environmental parameters for each of the sections; and
said control server is configured to, for each of the sections, obtain a representative parameter based on at least the environmental parameters obtained by said movable sensor module for the section;
said control server is configured to assign one of a plurality of states to each of the sections, the plurality of states including at least a normal state and an abnormal state;
wherein said control server is configured to sort the representative parameters for the sections, to assign a preset number of the sections having the highest representative parameter among all the sections with the abnormal state, and to assign the remaining ones of the sections with the normal state.

21. The system of claim 20, wherein for each of the sections, a sentinel is selected to obtain at least one health parameter, the health parameter being obtained from voiceprint data of the sentinel, a body temperature of the sentinel, and an image of a cloacae of the sentinel;
wherein said control server is configured to, for each of the sections, obtain a representative parameter further based on the health parameter of the sentinel for the section.

22. The system of claim 20, wherein the poultry house includes a plurality of cages for containing laying hens, and each of the sections is defined to cover at least one cage;
wherein one stationary sensor module is disposed in each of the sections.

23. An artificial intelligence system being for use in a plurality of poultry houses in different geographical regions, comprising, for each of the poultry houses:
a control server;
a network gateway disposed in the poultry house and equipped with a wireless communication capability;
a movable sensor module disposed in the poultry house, wherein said movable sensor module is movable within the poultry house for obtaining a plurality of environmental parameters associated with specific locations within the poultry house; and
a sampling machine disposed in the poultry house for obtaining a sample of poultry waste on the ground of the poultry house;
wherein said movable sensor module is in communication with said network gateway to transmit the environmental parameters to said network gateway, and said network gateway is configured to transmit the environmental parameters to said control server for processing the environmental parameters;
wherein said system further comprises, for each of the poultry houses, a mass spectrometer, a plurality of feeding machineries, and a movable conveying machine;
wherein, when it is determined that the environmental parameters are abnormal, said control server controls said sampling machine to obtain the sample of poultry waste at a location of said movable sensor module;
after obtaining the sample of poultry waste, said control server controls said sampling machine to provide the sample of poultry waste to said mass spectrometer for determining whether the sample of poultry waste contains a specific fecal bacteria;
wherein, when said control server determines that the sample of poultry waste contains a specific fecal bacteria, said control server controls said movable conveying machine to provide a medicine to one of the feeding machineries that corresponds to the location of said movable sensor module;
the system comprises a plurality of said movable sensor modules, each for a respective one of the poultry houses,
for each of the poultry houses, said movable sensor module is configured to obtain the environmental parameters for the poultry house;
said control server is configured to, for each of the poultry houses, obtain a representative parameter based on at least the environmental parameters obtained by said movable sensor module for the poultry house;
wherein said control server is configured to sort the representative parameters for the poultry houses, to assign a preset number of poultry houses having the highest representative parameter with the abnormal state, and to assign the remaining ones of the poultry houses with the normal state;
wherein said control server is further configured to determine, based on at least the spatial distribution of the poultry houses with the abnormal state, whether a disease is spreading among the poultry houses.

24. The system of claim 23, wherein:
when it is determined that a disease is spreading among the poultry houses, said control server is further configured to assign a level of alert to the poultry houses, and to generate a control signal based on the level of alert for performing a control protocol; and
wherein, when one of the poultry houses is assigned a level of alert indicating that a disease may be in an advanced stage of outbreak within the poultry house, the control server is configured to further transmit an alert to another of the poultry houses that is in proximity of the one of the poultry houses.

25. The system of claim 23, wherein for each of the poultry houses, a sentinel is selected to obtain at least one health parameter, the health parameter being obtained from voiceprint data of the sentinel, a body temperature of the sentinel, and an image of a cloacae of the sentinel;

wherein said control server is configured to, for each of the poultry houses, obtain a representative parameter further based on the health parameter of the sentinel for the poultry house.

* * * * *